United States Patent [19]

Szántay et al.

[11] 4,400,514
[45] Aug. 23, 1983

[54] PROCESS FOR THE PREPARATION OF APOVINCAMINIC ACID ESTER DERIVATIVES

[75] Inventors: Csaba Szántay; Lajos Szabó; György Kalaus; Lajos Dancsi; Tibor Keve; Ferenc Drexler; Krisztina Mihalyfi, all of Budapest, Hungary

[73] Assignee: Richter Gedeon Vegyeszeti Gyar Rt., Budapest, Hungary

[21] Appl. No.: 209,265

[22] Filed: Nov. 21, 1980

[30] Foreign Application Priority Data

Nov. 23, 1979 [HU] Hungary ................................ RI 735

[51] Int. Cl.³ .......................................... C07D 461/00
[52] U.S. Cl. ...................................................... 546/51
[58] Field of Search ............................................ 546/51

[56] References Cited

U.S. PATENT DOCUMENTS 2,797,221 6/1957 Gates, Jr. ............................ 546/44 X
4,283,401 8/1981 Szantay et al. .................... 546/51 X
4,315,011 2/1982 Szantay et al. .................... 546/51 X

FOREIGN PATENT DOCUMENTS 2819886 11/1978 Fed. Rep. of Germany ........ 546/51
53-147100 12/1978 Japan .

OTHER PUBLICATIONS

Wagner, et al., Synthetic Organic Chemistry, John Wiley & Sons, Inc., New York (1953).

Primary Examiner—Donald G. Daus
Assistant Examiner—Diana G. Rivers
Attorney, Agent, or Firm—Karl F. Ross; Herbert Dubno

[57] ABSTRACT

The invention concerns a new process for the preparation of apovincaminic acid ester derivatives of the general formula (I)

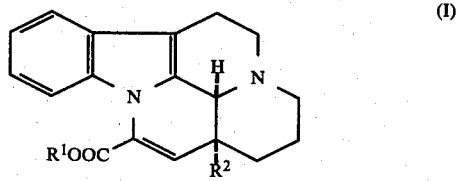

(I)

wherein
$R^1$ and $R^2$ independently represent an alkyl group having 1 to 6 carbon atoms,
and pharmaceutically acceptable salts thereof.

According to the invention the apovincaminic acid ester derivatives of the general formula (I) are prepared by reacting the corresponding 9- and/or 10- and/or 11-halo-14-oxo-15-hydroxyimino-E-homo-eburnane derivatives with an alkanol of the general formula $R^1$—OH, wherein $R^1$ is as defined above, and with a dehydrating concentrated acid, and subsequently reducing the 9- and/or 10- and/or 11-halo-apovincaminic acid esters obtained, selectively on the aromatic ring. Alternatively, the 9- and/or 10- and/or 11-halo-apovincaminic acid esters can also be used as starting materials. The invention includes the preparation of racemic and optically active apovincaminic acid ester derivatives and of their pharmaceutically acceptable salts, as well.

8 Claims, No Drawings

PROCESS FOR THE PREPARATION OF APOVINCAMINIC ACID ESTER DERIVATIVES

The invention relates to a new process for the preparation of apovincaminic acid derivatives. More particularly, the invention concerns a new process for the preparation of racemic or optically active apovincaminic acid ester derivatives of the formula (I)

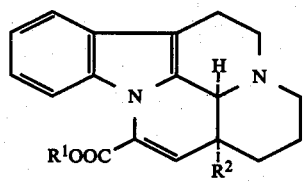

(I)

wherein
$R^1$ and $R^2$ each represent an alkyl group having 1 to 6 carbon atoms, and pharmaceutically acceptable salts thereof (a₁) by reacting a racemic or optically active 9- and/or 10- and/or 11-halo-14-oxo-15-hydroxyimino-E-homoeburnane derivative of the formula (IIIa)

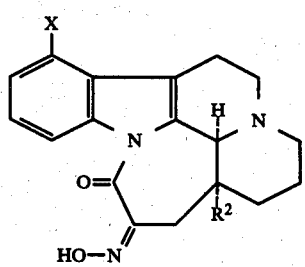

(IIIa)

and/or (IIIb)

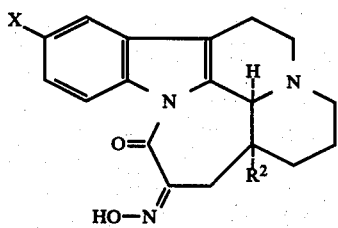

(IIIb)

and/or (IIIc)

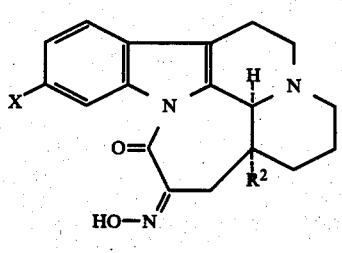

(IIIc)

wherein
$R^2$ has the same meaning as defined above and
X stands for a halogen atom,
or a pharmaceutically acceptable salt thereof, with an alkanol of the formula $R^1OH$, wherein $R^1$ is as defined above, and with a dehydrating concentrated acid, and subsequently reducing a 9- and/or 10- and/or 11-halo-apovincaminic acid ester of the formula (IIa)

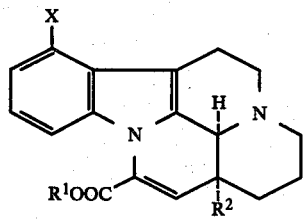

(IIa)

and/or (IIb)

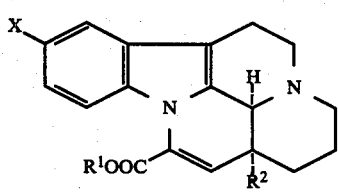

(IIb)

and/or (IIc)

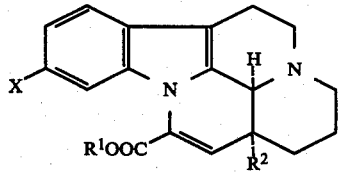

(IIc)

wherein $R^1$, $R^2$ and X have the same meaning as defined above, or an acid addition salt thereof, obtained selectively on the aromatic ring; or (a₂) by reducing a racemic or optically active halo-apovincaminic acid ester of the formula (IIa) and/or (IIb) and/or (IIc), wherein $R^1$, $R^2$ and X have the same meaning as defined above, or an acid addition salt thereof, selectively on the aromatic ring, and if desired, treating an apovincaminic acid ester derivative of the formula (I), wherein $R^1$ and $R^2$ are as defined above, prepared according to any one of process variants (a₁) and (a₂) with an acid suitable for preparing an acid addition salt and/or subjecting same to resolution.

The apovincaminic acid ester derivatives of the formula (I) possess valuable pharmaceutical properties. (+)-Apovincaminic acid ethyl ester for example shows outstanding cerebral vasodilating activity.

The term "alkyl group having 1 to 6 carbon atoms" used throughout the specification relates to straight or branched chained saturated aliphatic hydrocarbon groups having 1 to 6 carbon atoms, e.g. methyl, ethyl, n-propyl, isopropyl, n-butyl, isobutyl, tert.-butyl, n-pentyl, isopentyl, n-hexyl or isohexyl.

The starting compounds of the formula (IIa), (IIb) and (IIc) are also pharmaceutically active, more particularly, are capable of protecting the brain from damages due to anoxia. In these formulae the term "halogen" refers to fluorine, chlorine, bromine or iodine. Some compounds of the formulae (IIa), (IIb), and (IIc) can for example be prepared by brominating the corresponding 14-oxo-E-homo-eburnane derivatives and subsequently nitrosating the mixture of the 9-, 10- and 11-bromo-14-oxo-E-homo-eburnane derivatives obtained, without separation. The mixture of the 9-, 10- and 11-bromo-14-oxo-15-hydroxyimino-E-homo-eburnane intermediates of the formulae (IIIa), (IIIb) and (IIIc) is then subjected to selective crystallization. The separated compound of the formula (IIIa), (IIIb) or (IIIc) is reacted with an alkanol of the formula $R^1$—OH, wherein $R^1$ is as defined above, and with a dehydrating concentrated acid to yield the corresponding apovincaminic acid ester of the formula (IIa), (IIb), or (IIc).

Since by selective crystallization of a mixture of the compounds of the formula (IIIa), (IIIb) or (IIIc) always only one of the isomers is separated in a pure form, the mother liquor actually contains a certain amount from all three isomers. Although the isomeric mixture obtained by evaporating the mother liquor can be subjected to further selective crystallizations, i.e. can be recycled into the appropriate stage of synthesis, up to the present this isomeric mixture as such has practically not been utilized. The present invention provides a simple method for the utilization of this isomeric mixture on an industrial scale.

It has been found that by reacting an optional mixture of the compounds of the formulae (IIIa), (IIIb) and (IIIc) with an alkanol of the formula $R^1$—OH and a dehydrating concentrated acid, without previous separation, a mixture of the compounds of the formulae (IIa), (IIb) and (IIc) is obtained. In spite of the fact that each of the compounds of the formulae (IIa), (IIb) and (IIc) shows valuable pharmaceutical activities, their separation is rather cumbersome and accordingly, is not economic. It is therefore much more favorable to subject the mixture of these components to selective hydrogenation, when the 9-, 10- and 11-halogen atom is replaced by hydrogen, but the ring double bond remains unchanged. In this way from the mixture of three components a single, well-defined compound is obtained, corresponding to the formula (I). The compound possesses valuable cerebral vasodilating properties.

The present invention provides a new process for the preparation of the pharmaceutically active compounds of the formula (I), which can easily be accomplished on an industrial scale. In this respect the invention is a valuable contribution to the development of technology. A further advantage consists in the fact that according to the invention by a single synthesis route two different classes of pharmaceutically active compounds can be prepared, namely the halo-apovincaminic acid ester derivatives of the formulae (IIa), (IIb) and (IIc) and the apovincaminic acid esters of the formula (I). Finally, the process according to the invention provides a good possibility for the utilization of the by-products (isomeric mixtures) formed during the preparation of other pharmaceutically active compounds. The fact that the utilization of the by-product can take place in the next to the last step of the synthesis is also highly advantageous.

According to a further important feature of the invention the reaction conditions under which a halogen atom attached to the aromatic ring of the compounds of the formulae (IIa), (IIb) and (IIc) in an optional position can be replaced by a hydrogen atom without saturating the double bonds present in the ring, including the selection of an appropriate catalyst, are determined.

In addition to a selective reduction of a mixture of the compounds of the formula (IIa), (IIb) and (IIc) on the aromatic ring, the invention also includes the selective reduction of the compounds of the formula (IIa) or (IIb) or (IIc) alone.

The invention further includes the selective reduction of the compounds of the formula (IIa) and/or (IIb) and/or (IIc) independent thereof if these compounds have been prepared from a mixture of the compounds of the formulae (IIIa), (IIIb) and (IIIc) or from isolated compounds of the formulae (IIIa), (IIIb) and (IIIc), respectively, or in any other way.

As the dehydrating concentrated acid a dehydrating concentrated inorganic acid, such as concentrated sulfuric acid or polyphosphoric acid; or an anhydrous organic acid, such as anhydrous oxalic acid or p-toluenesulfonic acid can be used. The reaction is carried out in an alcohol of the formula $R^1$—OH, wherein $R^1$ is identical with the $R^1$ group which is to be incorporated into the compound.

According to a preferred embodiment of the invention a compound of the formula (IIIa) and/or (IIIb) and/or (IIIc) is reacted with a concentrated aqueous sulfuric acid solution in ethyl alcohol.

The reaction temperature and the reaction time depend on the dehydrating concentrated acid used and the medium of the formula $R^1$—OH.

The selective reduction of the compounds of the formulae (IIa) and/or (IIb) and/or (IIc) can be accomplished by a reducing agent, which is capable of replacing a halogen atom attached to an aromatic ring in an optional position without saturating the double bonds of the aromatic ring. The selective reduction is preferably carried out with catalytically activated hydrogen. As the hydrogenating catalyst, metals such as palladium, platinum, nickel, iron, copper, chromium, zinc, molybdenum, tungsten, ruthenium and oxides of these metals can be used. Catalysts precipitated on the surface of a carrier can also be employed. Suitable carriers include charcoal, alkali earth metal carbonates, such as calcium carbonate, alkali earth metal oxides, such as alumina, etc. The selection of the catalyst always depends on the hydrogenating substance and the reaction conditions.

The selective reduction can be performed in an inert solvent, such as water, aliphatic alcohols having 1 to 6 carbon atoms, e.g. methanol, ethanol, etc., alkanecarboxylic acids having 1 to 6 carbon atoms, such as glacial acetic acid; $C_{1-6}$-alkylesters of alkanecarboxylic acids having 1 to 6 carbon atoms, such as ethyl acetate; cyclic ethers, such as tetrahydrofuran, dioxane, etc., or in a mixture of said solvents.

The selective reduction carried out in the presence of a palladium, platinum or ruthenium catalyst can also be performed in an excess of a proton donor or in a mixture of a proton donor and one of the solvents listed above. As a proton donor preferably an organic compound, e.g. a dilute aqueous formic acid solution, cyclohexene; or an inorganic compound, e.g. hydrazine can be employed.

The selective reduction is accomplished under moderate reaction conditions and atmospheric pressure. The reaction temperature can be varied between 0° C. and 60° C., but preferably is between 20° C. and 25° C. The reaction time depends on the reaction temperature, the catalyst and the compound to be reduced. The reaction is preferably continued until 1.05 to 1.2 molar equivalents of hydrogen are consumed. The reaction is then terminated.

According to a preferred embodiment of the process according to the invention the selective reduction of the aromatic ring of the compounds of the formulae (IIa) and/or (IIb) and/or (IIc) is carried out in the presence of palladium-on-charcoal catalyst, in ethyl alcohol, under atmospheric pressure and at room temperature, until one molar equivalent of hydrogen is taken up.

The racemic or optically active compounds of the formula (I) prepared according to the invention, if desired, can be subjected to further purification steps, for example recrystallization.

The racemic or optically active compounds of the formula (I) prepared according to the invention if desired, can be converted into the pharmaceutically acceptable acid addition salts thereof. Suitable acids include inorganic acids, such as hydrogen halides, e.g. hydrochloric acid, hydrogen bromide, etc., sulfuric acid, phosphoric acid; perhalogenic acids, such as perchloric acid; or organic carboxylic acids, e.g. formic acid, acetic acid, propionic acid, oxalic acid, glycolic acid, maleic acid, fumaric acid, tartaric acid, succinic acid, ascorbic acid, citric acid, malic acid, salicylic acid, lactic acid, benzoic acid, cinnamic acid; alkylsulfonic acids, e.g. methanesulfonic acid; arylsulfonic acids, e.g. p-toluenesulfonic acid; cyclohexylsulfonic acids; asparaginic acid, glutamic acid, N-acetyl-asparaginic acid, N-acetyl-glutamic acid, etc.

The salts are preferably prepared in a reaction inert organic solvent, preferably in an aliphatic alcohol having 1 to 6 carbon atoms, such as methanol. More particularly a base of the formula (I) is dissolved in the said solvent and a corresponding acid is added until the pH of the reaction mixture becomes slightly acidic (about pH 6). The salt of a compound of the formula (I) is then isolated from the reaction mixture by precipitation with a water-immiscible organic solvent, such as diethyl ether.

The process according to the invention also includes the separation of the optically active isomers. The compounds are resolved by techniques known in the art. The resolution can be performed as a last step of the process according to the invention or alternatively, optically active starting compounds of the formulae (IIa) and/or (IIb) and/or (IIc) or (IIIa) and/or (IIIb) and/or (IIIc) can be employed. Finally, also the intermediates of the process can be subjected to resolution, and the subsequent reaction steps can be carried out with the optically active compounds obtained.

By the process according to the invention compounds of the formula (I) can be prepared with a high yield, in a well-identifiable form.

The process according to the invention is further illustrated by the following Examples. It is, however, by no means intended to limit our invention to the Examples.

EXAMPLE 1

The preparation of (+)-apovincaminic acid ethyl ester 1.0 g. of (+)-11-Bromo-apovincaminic acid ethyl ester is dissolved in 20 ml. of ethanol and to the solution 0.2 g. of a 10% by weight palladium-on-charcoal catalyst are added. The mixture is then hydrogenated under atmospheric pressure, at room temperature with stirring for 2 hours. The hydrogen consumption is 60 ml.

The catalyst is filtered off, and the filtrate is evaporated to dryness. The residual oil is dissolved in 10 ml. of methylene chloride, the solution is shaken with a 5% aqueous ammonium hydroxide solution, and the phases are separated. The organic phase is dried over solid, anhydrous sodium sulfate, filtered and the filtrate is evaporated to dryness.

The residual oil is treated with 2 ml. of ethanol, the crystals obtained are filtered off, washed with two 1-ml. portions of cold ethanol and are subsequently dried.

Thus 0.65 g. of (+)-apovincaminic acid ethyl ester are obtained as a white crystalline substance.

Yield: 79.6%.

Melting point: 149° C. to 151° C.

Specific rotatory power: $[\alpha]_D^{20} = +143°$ (c=1, chloroform).

The physical characteristics of the substance obtained are identical with those of a standard sample of (+)-apovincaminic acid ethyl ester.

EXAMPLE 2

Preparation of (+)-apovincaminic acid ethyl ester

Following the procedure described in Example 1 but starting from 0.5 g. of (+)-9-bromo-apovincaminic acid ethyl ester, 0.3 g. of (+)-apovincaminic acid ethyl ester are obtained.

Yield: 73.5%.

The physical characteristics of the substance obtained are identical with the corresponding characteristics of the product of Example 1 and with a standard sample of (+)-apovincaminic acid ethyl ester.

EXAMPLE 3

Preparation of (+)-apovincaminic acid ethyl ester

A mixture of 7.0 g. of (+)-9-bromo-14-oxo-15-hydroxyimino-E-homo-eburnane hydrochloride and (+)-11-bromo-14-oxo-15-hydroxyimino-E-homo-eburnane hydrochloride is heated in a mixture of 140 ml. of dry ethanol and 49 ml. of concentrated aqueous sulfuric acid at 90° C., under nitrogen atmosphere for 6 hours. The reaction mixture is then poured onto 500 ml. of ice water whereupon the pH of the mixture is adjusted to 9 with a 25% aqueous ammonium hydroxide solution. The alkaline solution is extracted with three 140-ml. portions of dichloromethane, the organic phase is separated, dried over solid, anhydrous sodium sulfate, filtered and the filtrate is dried.

Thus 6.5 g. of a mixture of (+)-9-bromo-apovincaminic acid ethyl ester and (+)-11-bromo-apovincaminic acid ethyl ester are obtained as an oily substance. The product is then subjected to selective reduction as described in Example 1.

3.2 g. of (+)-apovincaminic acid ethyl ester are obtained as a crystalline substance.

Yield: 59% (related to a mixture of 9- and 11-bromo-14-oxo-15-hydroxyimino-E-homo-eburnane).

Melting point: 148°–150° C.

Specific rotatory power: $[\alpha]_D^{20} = +138°$ (c=1, chloroform).

We claim:

1. A process for the preparation of a compound of the formula (I) in racemic or optically active form (I)

or a pharmaceutically acceptable acid addition salt thereof, wherein $R^1$ and $R^2$ are independently each $C_1$ to $C_6$ alkyl, which comprises the step of:

selectively hydrogenating at least one compound of the formula (IIa), (IIb) and (IIc)

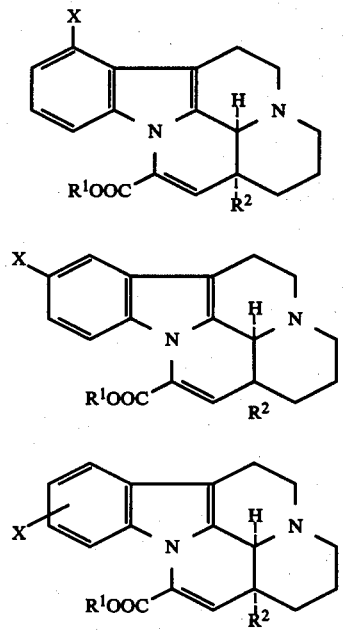

(IIa)

(IIb)

(IIc)

in a racemic or optically active form, wherein
X is halogen, or a pharmaceutically acceptable acid addition salt thereof, in the presence of a hydrogenation catalyst at a temperature of 0° to 60° C., to yield the desired product.

2. The process defined in claim 1 wherein the hydrogenation catalyst is precipitated on the surface of a carrier.

3. The process defined in claim 1 wherein palladium-on-charcoal is used as the hydrogenation catalyst.

4. The process defined in claim 1 wherein the hydrogenation is carried out in an inert solvent.

5. The process defined in claim 1 wherein the temperature is 20° to 25° C.

6. The process defined in claim 1 wherein 1.05 to 1.2 molar equivalents of hydrogen are taken up.

7. The process defined in claim 1 wherein 1 molar equivalent of hydrogen is taken up.

8. The process defined in claim 1 wherein the compound of the formulae (IIa), (IIb) or (IIc) are obtained by reacting at least one compound of the formulae (IIIa), (IIIb) and (IIIc)

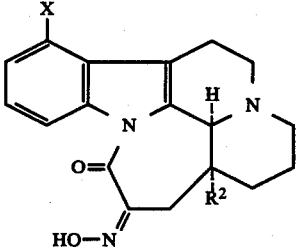

(IIIa)

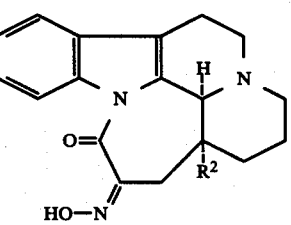

(IIIb)

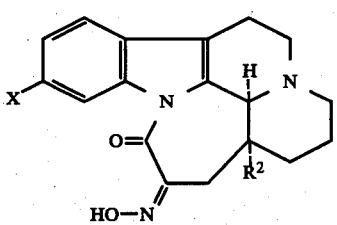

(IIIc)

in racemic or optically active form, or a pharmaceutically acceptable acid addition salt thereof, with a dehydrating concentrated acid and an alcohol of the formula $R^1$—OH wherein $R^1$ is $C_1$ to $C_6$ alkyl.

* * * * *